United States Patent [19]

Gotoh et al.

[11] Patent Number: 5,493,597
[45] Date of Patent: Feb. 20, 1996

[54] X-RAY DIAGNOSTIC APPARATUS AND X-RAY DIAGNOSTIC METHOD

[75] Inventors: Atsushi Gotoh, Tochigi; Shuzo Yamamoto, Ibaraki; Teruomi Gunji, Ootawara, all of Japan

[73] Assignee: Kabushiki Kaisha Toshiba, Kawasaki, Japan

[21] Appl. No.: 302,265

[22] Filed: Sep. 8, 1994

[30] Foreign Application Priority Data

Sep. 10, 1993  [JP]  Japan ................................ 5-225334
Dec. 28, 1993  [JP]  Japan ................................ 5-334388

[51] Int. Cl.⁶ .................................................... A61B 6/00
[52] U.S. Cl. ........................... 378/98.2; 378/147; 378/152
[58] Field of Search ............................ 378/98.2, 98, 62, 378/147, 150, 152, 167, 193, 195, 196, 197, 198

[56] References Cited

U.S. PATENT DOCUMENTS 4,674,107  6/1987  Urban et al. .................... 378/98.2 X
4,937,848  6/1990  Horbaschek et al. ................ 378/98.2
5,159,622  10/1992  Sakaniwa et al. .
5,367,554  11/1994  Kobayashi et al. ................... 378/196

*Primary Examiner*—David P. Porta
*Attorney, Agent, or Firm*—Oblon, Spivak, McClelland, Maier & Neustadt

[57] ABSTRACT

A triaxially controlled X-ray diagnostic apparatus comprises a support unit having a first arm, a second arm, and a third arm which are capable of rotation on three mutually orthogonal axes, an X-ray generator mounted on an end of the third arm for irradiating an object under examination with X rays, an image intensifier, mounted on the other end of the third arm so that it is opposed to the X-ray generator, for detecting X rays transmitted through the object to provide an optical image, a TV camera connected to the image intensifier for converting the optical image into a video signal to provide an X-ray image of the object, a display unit for displaying the X-ray image, and rotation correction means for making rotation correction on an X-ray image displayed on the display unit on the basis of angles of rotation of the first, second and third arms when they are rotated from their reference position.

11 Claims, 5 Drawing Sheets

X-RAY DIAGNOSTIC APPARATUS AND X-RAY DIAGNOSTIC METHOD

BACKGROUND OF THE INVENTION

1. Field of the Invention

The present invention relates to an X-ray diagnostic apparatus and X-ray diagnostic method, and more particularly to rotation correction of observed images and display control of an X-ray beam limiting device in an X-ray diagnostic apparatus in which an X-ray generator and so on are carried on a triaxially controlled support unit.

2. Description of the Related Art

In an X-ray diagnostic apparatus, a triaxially controlled support unit is known which carries an X-ray generator for irradiating an object under examination with X-rays, an image intensifier disposed opposite the X-ray generator for detecting X-rays transmitted through the object to provide an optical image, and a TV camera for converting the optical image into a video signal to provide an X-ray image of the object. The X-ray generator, the image intensifier and the TV camera are adapted to rotate on three axes which are orthogonal to one another while keeping their relative position.

FIG. 1 is a schematic illustration of this triaxially controlled support unit.

In this figure, the support unit 40 carries an X-ray generator 10, an image intensifier 20 which are opposed to each other with an object under examination 15 interposed therebetween, and a TV camera 30 connected to the image intensifier 20 and rotates on three mutually orthogonal axes intersecting at the arm center O. In addition to the support unit 40, FIG. 1 shows, in block form, signal processing circuitry for processing a video signal output from the TV camera 30. The video signal is converted to a digital signal by an analog-to-digital (A/D) converter 32, then subjected to imaging processing in an image processing unit 34, converted to an analog signal in a digital-to-analog (D/A) converter 36, and visually displayed on a display unit 38. A rotation correction unit 48 corrects the rotation of the arm, etc., which will be described later in detail.

The first rotation axis is perpendicular to the plane including the arm 42 and passes through the arm center O. Sliding the arm 42 relative to an arm column 44 causes the support unit 40 to rotate around the first rotation axis in the direction indicated by an arrow $\alpha$. Hereinafter, this angle of rotation is referred to as an arm slide angle, which is indicated by $\alpha$. The second rotation axis corresponds to the arm column 44 itself that rotates in the direction of an arrow $\beta$. The angle of rotation of the second axis is referred to as an arm rotating angle, which is indicated by $\beta$. The third rotation axis corresponds to the column 46 of the main body of the support unit, which rotates in the direction of an arrow $\gamma$. The angle of rotation of the third axis is referred to as an column rotating angle, which is indicated by $\gamma$.

An X-ray image of the object under examination 15 obtained when the triaxially controlled support unit 40 is set in the reference position is called a "vertical image". The angles of each rotation axis at that point are defined as 0° (i.e., $\alpha=\beta=\gamma=0°$).

When the support unit 40 revolves on each of the three axes through an angle, the rotation correcting unit 48 rotates the TV camera 30 (more accurately, its head) so that a vertical image can be obtained. For example, when the arm 42 is shifted from the head side of the object under examination 15 or from the side of the object for X-ray photography, the TV camera 30 is controlled to rotate through an angle $\phi$ equal to an column rotating angle $\gamma$ so that resulting X-ray images of the object are directed in the same direction, that is, vertical images of the object can be obtained.

In the prior art, the column rotating angle $\gamma$ is considered, but the two other angles associated with the support unit, i.e., the arm slide angle $\alpha$ and the arm rotating angle $\beta$, are not taken into consideration in rotation correction. For this reason, vertical images can be obtained when only the column 46 is rotated. However, when other columns than the column 46 are rotated, correction of an image cannot be made for that rotation. Thus, there arises the possibility that no vertical images may be obtained. That is, when the two other axes are rotated with the column rotating angle $\gamma$ set at any value, no vertical images can be obtained even if the TV camera 30 is rotated for correction. Thus, even if a comparison is made between a past reference X-ray image and a current X-ray image which have been captured at the same clinical angle, they will look rotated with respect to each other, which involves difficulties in making comparative diagnosis.

Even when the above problems are solved, since the image rotation correction is made only by rotating the TV camera, a problem will arise in that the direction in which an X-ray beam limiting device (including a compensation filter) displayed on the display unit opens or closes and the direction in which the X-ray beam limiting device opens or closes as instructed by a movement operation switch may not coincide with each other. This problem will be described in detail with reference to FIGS. 2A, 2B and 2C.

FIGS. 2A, 2B and 2C show an image 15' of an object and an image 12' of the X-ray beam limiting device displayed on the display unit 38, which are obtained as a result of the conventional image rotation correction method. More specifically, FIG. 2A shows images obtained prior to rotation of the support unit (that is, when the support unit is placed in the reference position), FIG. 2B shows images obtained after the rotation of the support unit but before rotation correction, and FIG. 2C shows images after the images of FIG. 2B have been subjected to rotation correction. In the figures, arrows A1, A2 and A3, which are displayed on the display unit 38, indicate the direction of movement of the X-ray beam limiting device when it is instructed to close in the left/right direction by the X-ray beam limiting device movement operation switch provided on an operating console not shown.

In the case of FIG. 2A where the support unit is set in the reference position, the image 15' of the object is displayed vertically and the image 12' of the X-ray beam limiting device is displayed on the right and left sides of the display unit 38. A 90° rotation of the support unit results in the images shown in FIG. 2B. In this case, the image 15' of the object is displayed rotated (tilted) through 90°, whereas the image 12' of the X-ray beam limiting device is displayed on the right and left sides of the display unit as in the case of FIG. 2A because the relative position of the X-ray beam limiting device and the TV camera remains unchanged. Thus, since the image 12' of the X-ray beam limiting device moves to close in the left/right direction as shown by the arrows A2 when an operation to close in the left/right direction is given by the operation switch, the direction in which the image 12' of the X-ray beam limiting device opens or closes coincides with the direction specified by the operation switch 52.

In the conventional X-ray diagnostic apparatus, in order to display the image 15' of the object as a vertical image, the TV camera is rotated through a predetermined angle with the rotation of the support unit to thereby make rotation correction on the image 15' of the object. The resulting image is shown in FIG. 2C. Though the image 15' of the object is displayed vertically, the image 12' of the X-ray beam limiting device is displayed rotated through 90° because the TV camera is rotated through 90° for correction. That is, the image 12' is displayed up and down. If, in the case of FIG. 2C, the operation switch is operated so as to close the X-ray beam limiting device in the right/left direction, then the image 12' of the X-ray beam limiting device will move up and down on the display unit as indicated by the arrows A3 because the TV camera is rotated through 90° with respect to the X-ray beam limiting device.

In the conventional triaxial-holding-device-based X-ray diagnostic apparatus in which the direction of movement of the X-ray beam limiting device instructed by the movement operation switch does not coincide with the direction in which the X-ray beam limiting device image on the display unit moves to open or close, therefore, problems arises in the case of image rotation correction in that maloperation may be caused and operation is troublesome.

As described above, the conventional support unit has the following problems.

(1) No match is found between a reference image obtained in the past at a given column rotating angle and an X-ray image being currently observed at the same column rotating angle, which makes comparative diagnosis difficult.

(2) The direction in which the X-ray beam limiting device displayed on the display unit moves to open or close does not coincide with the direction of movement of the X-ray beam limiting device instructed by the movement operation switch, which may cause maloperation and makes operation troublesome.

SUMMARY OF THE INVENTION

It is accordingly an object of the present invention to provide an improved X-ray diagnostic apparatus and X-ray diagnostic method.

More specifically, it is an object of the present invention, in a triaxial-holding-device-based X-ray diagnostic apparatus or a method applied thereto, is (1) obtaining vertical images all the time even if the angle of rotation of each axis is set at any value, and (2) coinciding the direction of movement of the X-ray beam limiting device displayed on the display unit with the direction of its movement instructed by an operation means to thereby make operation easy.

According to the first aspect of the present invention there is provided an X-ray diagnostic apparatus comprising: support means having a first arm capable of rotation on a first axis, a second arm attached to the first arm so that it can rotate on a second axis, and a third arm attached to the second arm so that it can slide on an arc centered at a third axis, the first, second and third arms having first, second and third reference positions, respectively; an X-ray generator mounted on an end of the third arm for irradiating an object under examination with X rays; an image intensifier, mounted on the other end of the third arm so that it is opposed to the X-ray generator, for detecting X rays transmitted through the object under examination to provide an optical image; a TV camera connected to the image intensifier for converting the optical image into a video signal to provide an X-ray image of the object; display means for displaying the X-ray image; and rotation correction means for, when the support unit rotates, making rotation correction an X-ray image displayed on the display means on the basis of a first rotation angle of said first arm from its first reference position, a second rotation angle of said second arm from its second reference position, and a third rotation angle of said third arm from its third reference position.

More specifically, assuming said first, second and third rotation angles to be $\alpha$, $\beta$ and $\gamma$, respectively, and taking $$X = \sin\alpha \cdot \cos\gamma - \sin\beta \cdot \cos\alpha \cdot \sin\gamma,$$

the rotation correction means makes rotation correction on the X-ray image by rotating it through an angle $\phi$, which is determined as follows:

(a) when $X=1$, $$\phi = 180 - \beta \, (\gamma=0)$$

$$\phi = \beta \, (\gamma \neq 0)$$

(b) when $X=-1$, $$\phi = 180 - \beta \, (\gamma = \pm 180)$$

$$\phi = \beta \, (\gamma \neq \pm 180)$$

(c) when $X \neq \pm 1$, $$\phi = \phi_0 \text{ when } \gamma \cdot \cos\beta > 0$$

$$\phi = -\phi_0 \text{ when } \gamma \cdot \cos\beta < 0$$

where $$\phi_0 = \cos^{-1}\{(\cos\gamma \cdot \cos\alpha + \sin\beta \cdot \sin\alpha \cdot \sin\gamma)/(1-X^2)^{1/2}\}.$$

The rotation correction means includes at least one of means for rotating the TV camera, means for rotating the image intensifier, and means for making image rotation correction by means of image processing.

An X-ray diagnostic method for use with the X-ray diagnostic apparatus of the first aspect of the present invention comprises the step of, when the support unit rotates, making rotation correction an X-ray image being displayed on the display means on the basis of a first rotation angle of the first arm from its first reference position, a second rotation angle of the second arm from its second reference position, and a third rotation angle of the third arm from its third reference position in such a way that the X-ray image is displayed in the same direction as an X-ray image obtained when the first arm is placed in the first reference position.

According to the first aspect of the present invention, in rotation correction of a reference image and an X-ray image (observed image), an arm slide angle and an arm rotating angle are allowed for in addition to a column rotating angle in the prior art. The image rotation correction includes the rotation of the TV camera head and the rotation by image processing. Thereby, at the same clinical angle, vertical images can be obtained all the time. This facilitates diagnosis based on a comparison between a reference image and an X-ray image and reduces the time required to make diagnosis. In addition, the image rotation correction can be made automatically without having to watch the display screen, which reduces X-ray exposure doses and the burden on an operator.

According to a second aspect of the present invention there is provided an X-ray diagnostic apparatus comprising: support means carrying an X-ray generator with an X-ray beam limiting device for irradiating an object under examination with X rays through the X-ray beam limiting device, an image intensifier opposed to the X-ray generator for detecting X rays transmitted through the object to provide an optical image, and TV camera for converting the optical image into a video signal to provide an X-ray image of the object, the X-ray generator, the image intensifier and the TV camera rotating about three mutually orthogonal axes while keeping their relative position; movement operation means for instructing the X-ray beam limiting device in first and second directions on a plane perpendicular to the direction of emission of X rays from the X-ray generator; display means for displaying an X-ray image of the object output from the TV camera; rotation correction means for correcting for the tilt of an X-ray image of the object displayed on the display means due to the rotation of the support unit; and correction means for making the direction of opening or closing of the X-ray beam limiting device displayed on the display means coincident with a direction of movement of the X-ray beam limiting device instructed by the movement operation means all the time.

The correction means includes means for rotating the X-ray beam limiting device through a given angle in a given direction in conjunction with the rotation of at least one of the TV camera and the image intensifier.

An X-ray diagnostic method for use with the X-ray diagnostic apparatus of the second aspect of the present invention comprises the step of making the direction of opening or closing of the X-ray beam limiting device displayed on the display means coincident with a direction of movement of the X-ray beam limiting device instructed by the movement operation means all the time.

In the above method, the X-ray beam limiting device is rotated through a given angle in a given direction in conjunction with the rotation of at least one of the TV camera and the image intensifier.

According to the second aspect of the present invention, the direction of movement of the X-ray beam limiting device displayed on the display device to open or close coincides with the direction of the movement of the X-ray beam limiting device specified by the operation switch on an operating console. Thus, maloperation can be avoided. This permits fast diagnosis and reduces the burden on an operator. The operator is allowed to move the X-ray beam limiting device at will, which improves the reliability of the apparatus.

Additional objects and advantages of the present invention will be set forth in the description which follows, and in part will be obvious from the description, or may be learned by practice of the present invention. The objects and advantages of the present invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the present invention and, together with the general description given above and the detailed description of the preferred embodiments given below, serve to explain the principles of the present invention in which.

Detailed Description of the Preferred Embodiments

An X-ray diagnostic apparatus generally includes an X-ray generator for irradiating an object under examination with X rays, an image intensifier placed opposite the X-ray generator for detecting X rays transmitted through the object to output an optical image, a TV camera for converting the optical image into a video signal to provide an X-ray image of the object, and a display unit for displaying the X-ray image of the object output from the TV camera.

Figure 1:
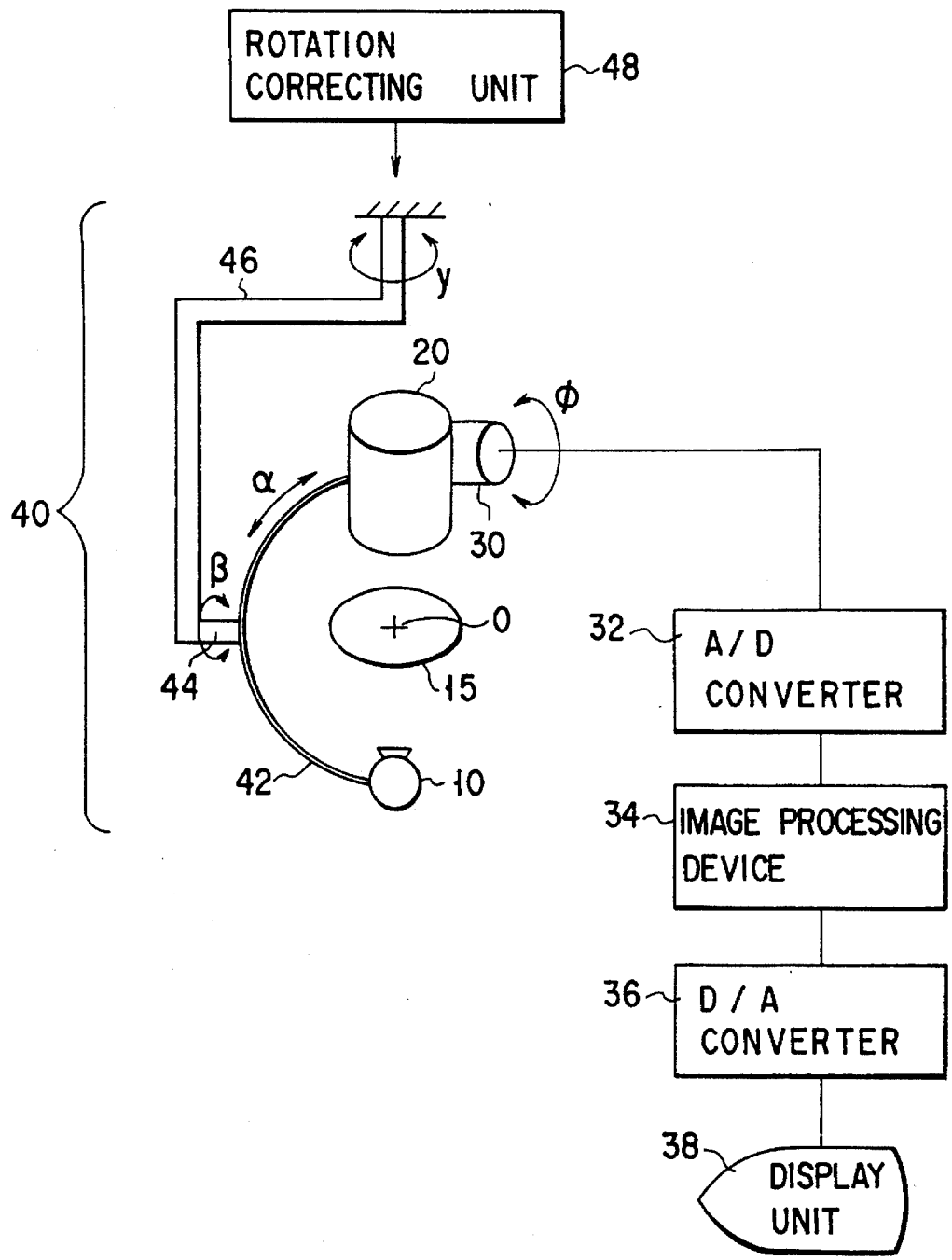
FIG. 1 is a simplified diagram of a triaxial support unit used in an X-ray diagnostic apparatus.

A type of X-ray diagnostic apparatus has a support unit which carries the X-ray generator, the image intensifier and the TV camera and rotates independently about each of three mutually orthogonal axes while keeping the relative position of these devices. The support unit according to a first embodiment of the present invention is similar in arrangement to that described in connection with FIG. 1, and hence the first embodiment will be described with reference to FIG. 1.

As described above, the support unit 40 rotates about each of three axes which are orthogonal to one another at the arm center O. The three axes are defined in the same manner as described above as follows. The first rotation axis is defined as an axis that is perpendicular to the plane involving the arm 42. When the arm 42 slides relative to the arm column 44, the support unit 40 will rotate about the first rotation axis. An angle of rotation of the support unit is referred hereinafter to as an arm slide angle (the symbol $\alpha$ is used therefor). The second rotation axis corresponds to the arm column 44. The angle of rotation of the support unit about the second rotation axis is referred hereinafter to as an arm rotating angle (the symbol $\beta$ is used therefor). The third rotation axis corresponds to the column 46 of the main body of the support unit 40. The rotation angle of the support unit about the third axis is referred hereinafter to as a column rotating angle (the symbol $\gamma$ is used therefor).

In addition, an image of the object 15 obtained when the above-described three-axis support unit 40 is placed in the reference position is referred to as a vertical image. The angles of each rotation angle at this point are defined as 0° (i.e., $\alpha=\beta=\gamma=0°$).

The image rotation correction performed when the arm slide angle $\alpha$, the arm rotating angle $\beta$, and the column rotating angle $\gamma$ are changed will be described below in detail.

When $\gamma=0°$, an X-ray image obtained is always vertical even if the arm slide angle $\alpha$ and the arm rotating angle $\beta$ are changed. In this case, therefore, there is no need of making any rotation correction on the image.

When $\gamma \neq 0°$, on the other hand, the image is not vertical. Thus, image rotation correction is required. In the case of X-ray examination at a clinical angle ($\gamma \neq 0°$), a vertical X-ray image will be obtained all the time by properly setting an angle of rotation $\phi$ (hereinafter referred to as an image rotation angle) of the TV camera 30 in a state where the arm slide angle $\alpha$, the arm rotating angle $\beta$, and the column rotating angle $\gamma$ have been changed.

The present invention is directed to an X-ray image rotating means (the rotation correction unit 48) for accurately setting the image rotation angle $\phi$ when each of the arm slide angle $\alpha$, the arm rotating angle $\beta$ and the column rotating angle $\gamma$ is changed arbitrarily.

In the present invention, the image rotation angle $\phi$ is obtained as follows. In the following expressions, the unit of angle is the degree.

Using the arm slide angle $\alpha$, the arm rotating angle $\beta$, and the column rotating angle $\gamma$, X is defined as follows:

$$X = \sin\alpha \cdot \cos\gamma - \sin\beta \cdot \cos\alpha \cdot \sin\gamma \quad (1)$$

In equation (1), when X=1 or X=−1, the image rotation angle $\phi$ does not depend on the arm slide angle $\alpha$.

(a) When X=1, $$\phi = 180 - \beta \, (\gamma = 0) \quad (2)$$

$$\phi = \beta \, (\gamma \neq 0) \quad (3)$$

(b) When X=−1, $$\phi = 180 - \beta \, (\gamma = \pm 180) \quad (4)$$

$$\phi = \beta \, (\gamma \neq \pm 180) \quad (5)$$

When X≠±1, on the other hand, the image rotation angle $\phi$ is obtained as follows:

$$\phi = \phi_0 \, (\beta \cos\gamma > 0) \quad (6)$$

$$\phi = -\phi_0 \, (\gamma \cos\beta < 0) \quad (7)$$

Here, $$\phi_0 = \cos^{-1}\{(\cos\gamma \cdot \cos\alpha + \sin\beta \cdot \sin\alpha \cdot \sin\gamma)/(1-X^2)^{1/2}\} \quad (8)$$

The specific positioning based on the above-described means will be described. In this case, suppose that diagnosis is made at clinical angles (CRA, LAO)=(30°, 60°).

It is supposed that images have been obtained at two sets of mechanical angles ($\alpha, \beta, \gamma$) for the clinical angles. The first image is a reference image at A (30°, 60°, 0°), whereas the second image is an X-ray image at B (64°, −8°, 60°).

Therefore, the rotation angles of the first and second images are $\alpha=30°, \beta=60°, \gamma=0°$ (reference image)

$\alpha=64°, \beta=-8°, \gamma=60°$ (X-ray image)

Figure 3A:
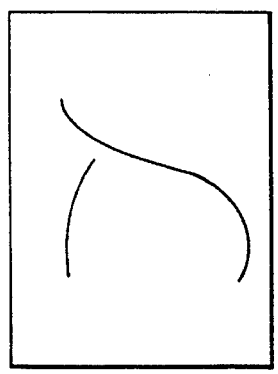
FIGS. 3A and 3B illustrate a reference image and an X-ray image corrected by the conventional image rotation correction technique.
Figure 3B:
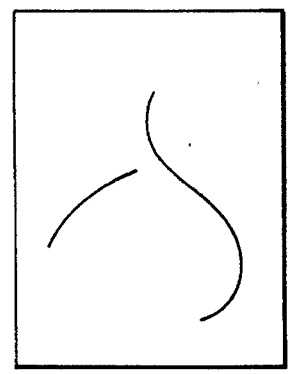

In the present embodiment, where the conventional positioning method is used, the image rotation angle $\phi$ will be 60° because $\phi=\gamma$. Thus, the TV camera requires to be rotated through 60° for image positioning. This state is illustrated in FIGS. 3A and 3B. FIG. 3A illustrates a reference image, whereas FIG. 3B illustrates an X-ray image that has been subjected to rotation correction. As can been seen from FIGS. 3A and 3B, in the conventional image positioning, the column rotating angle $\gamma$ is taken into consideration to set the image rotation angle $\phi$, but the arm rotating angle $\beta$ and the column rotating angle $\gamma$ are not taken into consideration, which results in inaccurate positioning. Thus, since a vertical image cannot be obtained even after image rotation correction has been made as shown in FIG. 3B, the reference image and the X-ray image do not match with each other in direction.

Examples of settings of the image rotation angle $\phi$ by the means of the present invention are indicated below. As described previously, the reference image and the X-ray image have been obtained at the rotation angles:

$\alpha=30°, \beta=60°, \gamma=0°$ (reference image)

$\alpha=64°, \beta=-8°, \gamma=60°$ (X-ray image)

The reference image is vertical since $\gamma=0°$ and requires no image rotation correction. Next, the X-ray image will be considered.

From equation (1), the value of X is calculated to be $X = \sin 64 \cdot \cos 60 - \sin(-8) \cdot \cos 64 \cdot \sin 60 = 0.52$ Since X≠±1, equation (8) is used to calculate $\phi_0$, which is calculated to be $$\phi = \cos^{-1}\{(\cos 60 \cdot \cos 64 + \sin(-8) \cdot \sin 64 \cdot \sin 60)/(1-X^2)^{1/2}\} = 82.6$$

And, since $\gamma \cdot \cos\beta = 60 \cdot \cos(-8) = 59 > 0$, the image rotation angle $\phi$ will be calculated from equation (6) to be $\phi = 82.6$ This value is rounded off to obtain $\phi=83°$.

Figure 4A:
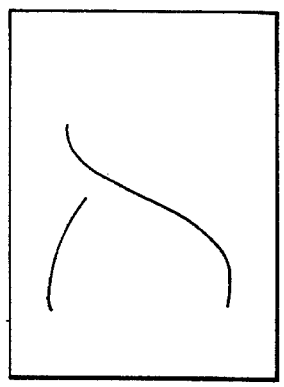
FIGS. 4A and 4B illustrate a reference image and an X-ray image subjected to image rotation correction of the present invention.
Figure 4B:
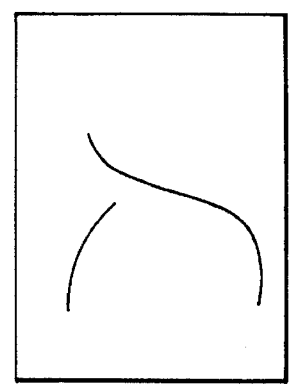

The result of the image rotation correction based on the image rotation angle $\phi$ thus obtained is illustrated in FIGS. 4A and 4B. FIG. 4A shows a reference image and FIG. 4B shows an X-ray image subjected to the rotational correction. From FIGS. 4A and 4B it will be understood that the present invention permits both the reference image and the X-ray image to be displayed vertically, that is, both the images are permitted to match with each other in direction. According to the present invention, therefore, an image is always displayed vertically on the display unit 38.

According to the present invention, even if at least one of the arm slide angle $\alpha$ and the arm rotating angle $\beta$ is changed in addition to the column rotating angle $\gamma$, a vertical image can be obtained all the time. Since both the reference image and the X-ray image are vertical, a comparison between them can be made easily, which permits fast diagnosis.

In addition, the image rotation correction is made automatically without watching the display unit 38, which reduces the X-ray exposure dose and lightens the burden on an operator.

The first embodiment has been described as capturing a vertical image by rotating the TV camera 30 through an image rotation angle. This is illustrative and not restrictive. The image intensifier may be rotated instead. Alternatively, an image may be rotated by the image processing unit 34 at the time of display on the display unit.

Figure 5A:
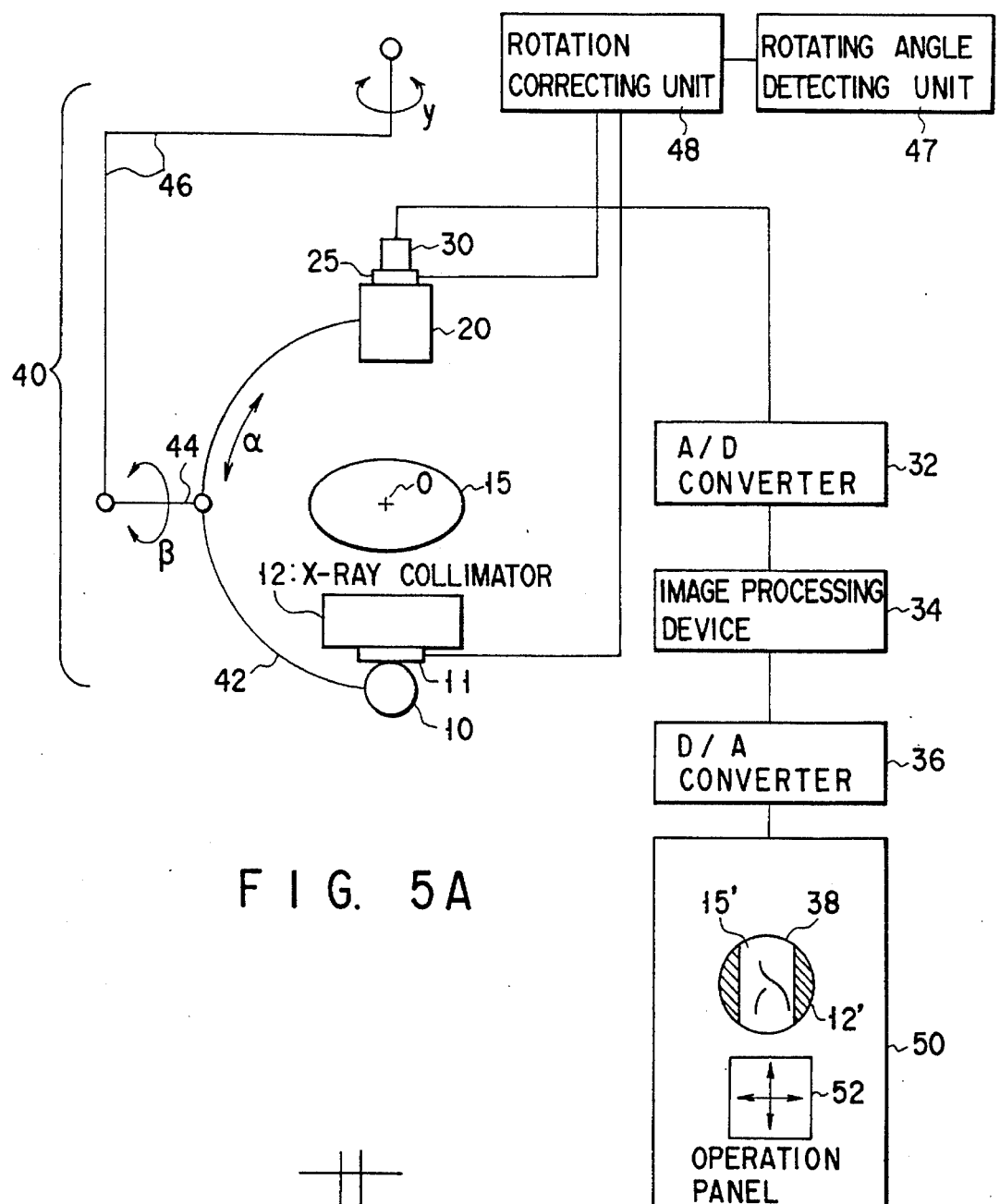
FIGS. 5A and 5B are simplified diagrams of an X-ray diagnostic apparatus according to a second embodiment of the present invention.
Figure 5B:
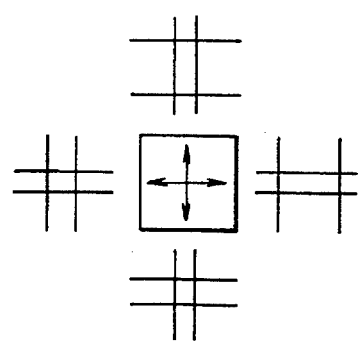

FIGS. 5A and 5B show an X-ray diagnostic apparatus according to a second embodiment of the present invention. More specifically, FIG. 5A is a simplified block diagram of the entire X-ray diagnostic apparatus, and FIG. 5B illustrates directions in which X-ray beam limiting device 12 is opened or closed as instructed by the movement operation switch 52.

In FIG. 5A, the support unit 40 carries an X-ray generator 10 having an X-ray beam limiting device 12 (including a compensation filter) for adjusting the energy distribution of X rays and a rotating device 11, incorporated in the X-ray beam limiting device 12, for rotating the X-ray beam limiting device, an image intensifier 20 opposed to the X-ray generator 10 with an object under examination 15 interposed therebetween, a TV camera 30 connected to the image intensifier, and a TV head rotating device 25 for rotating the head of the TV camera 30. The support unit rotates independently about each of the three mutually orthogonal axes which intersect at the arm center O.

In addition to the support unit 40, FIG. 5A shows simplified signal processing circuitry for processing a video signal output from the TV camera 30. A video signal from the TV camera 30 is converted into a digital signal in an A/D converter 32, then subjected to desired image processing in an image processing unit 34, converted into an analog signal in a D/A converter 36, and visually displayed on a display device 38 provided on an operating console 50. On the display unit 38 is displayed an image 12' of the X-ray beam limiting device in addition to an image 15' of the object under examination. The operating console 50 is also equipped with a movement operation switch 52 adapted for moving the X-ray beam limiting device 12 to open or close in a direction.

The switch 52 is a switch with a movable lever, for example. By moving the lever left, right, up, or down, the X-ray beam limiting device is instructed to open or close in a direction. To be specific, as shown in FIG. 5B, the X-ray beam limiting device is instructed to open in the up/down direction by moving the lever up, to close in the up/down direction by moving the lever down, to close in the left/right direction by moving the lever left, and to open in the left/right direction by moving the lever right. For example, therefore, when the lever of the switch 52 is moved left, the X-ray beam limiting device is instructed to close in the left/right direction. Thus, the X-ray beam limiting device moves to close in the left/right direction, so that the image 12' of the X-ray beam limiting device displayed left and right on the display device 38 moves to close in the left/right direction.

A rotation angle detector 47 detects an angle of rotation of the support unit 40 on each of the three mutually orthogonal axes.

A rotation correction unit 48 produces rotation correction signals on the basis of detected values by the rotation angle detector 47. More specifically, in order to make rotation correction on an image displayed on the display device 38 so that it can be displayed vertically, which is required due to rotation of the support unit on the three axes, the rotation correction unit 48 outputs to the X-ray beam limiting device rotating device 11 and the TV head driving device 25 control signals for controlling the rotation of the head of the TV camera 30 (hereinafter simply referred to as the TV camera) and the rotation of the X-ray beam limiting device 12 so that the X-ray beam limiting device can be moved in a direction instructed by the movement operation switch 52.

In the above-described support unit, the first rotation axis is perpendicular to the plane involving the arm 42 and passes through the arm center O. If the arm 42 slides relative to the arm column 44, then the support unit will rotate about the first rotation axis in a direction indicated by an arrow α. The second rotation axis corresponds to the arm column 44 and rotates in a direction indicated by an arrow β. The third rotation axis corresponds to the column 46 of the body of the support unit 40 and rotates in a direction indicated by an arrow γ.

The second embodiment of present invention features that the direction in which the image 12' of the X-ray beam limiting device displayed on the display device 38 moves to open or close is made to always coincide with the direction in which the X-ray beam limiting device is moved to open or close as operated by the X-ray movement operation switch 52 on the operating console 50. That is, according to the second embodiment of the present invention, the image 12' of the X-ray beam limiting device displayed on the display device 38 is moved to open in the left/right direction when the lever of the movement operation switch 52 is moved right, that is, the X-ray beam limiting device is instructed to open in the left/right direction, and when the X-ray beam limiting device is instructed to open in the up/down direction by the movement operation switch, it is moved to open in the up/down direction.

More specifically, in the second embodiment of the present invention, when the TV camera 30 is rotated through a given angle by the rotation correction unit 48 so as to obtain a vertical image, the X-ray beam limiting device 12 is rotated through an angle equal to the angle of rotation of the TV camera so that a relative relationship between the TV camera 30 and the X-ray beam limiting device 12 remains unchanged. As a result, the image 12' of the X-ray beam limiting device always stays in the same locations on the display device 38 (left and right in the figure), and the direction in which the X-ray beam limiting device 12 opens or closes coincides with the direction instructed by the movement operation switch 52.

The operation of the apparatus of the present invention constructed as described above will be described with reference to FIGS. 6A, 6B, and 6C.

Figure 2A:
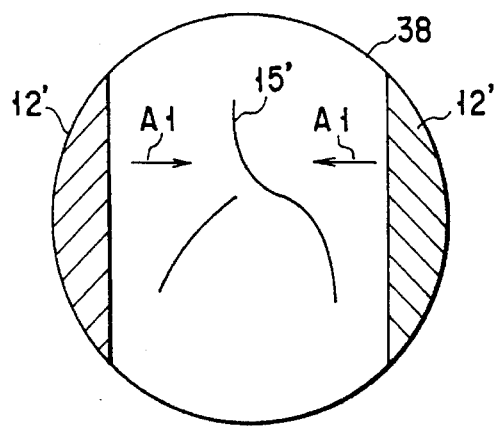
FIGS. 2A, 2B and 2C illustrate exemplary display images corrected by a conventional image rotation correction technique.
Figure 2B:
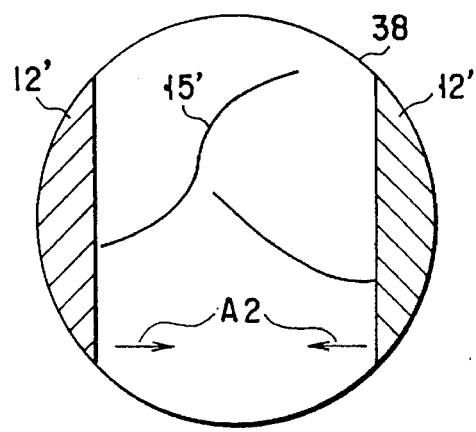
Figure 2C:
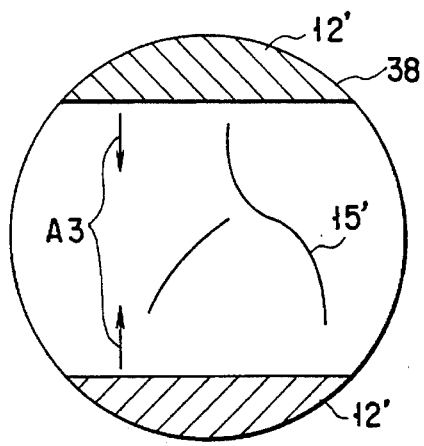
Figure 6A:
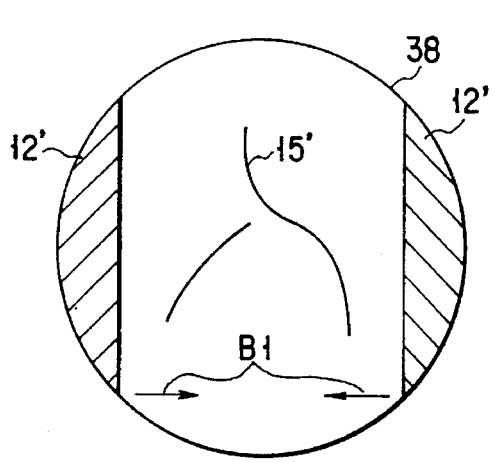
FIGS. 6A, 6B and 6C illustrate examples of images displayed on the display unit in accordance with the present invention.
Figure 6B:
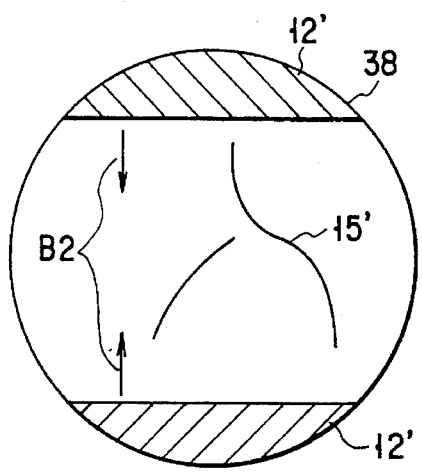
Figure 6C:
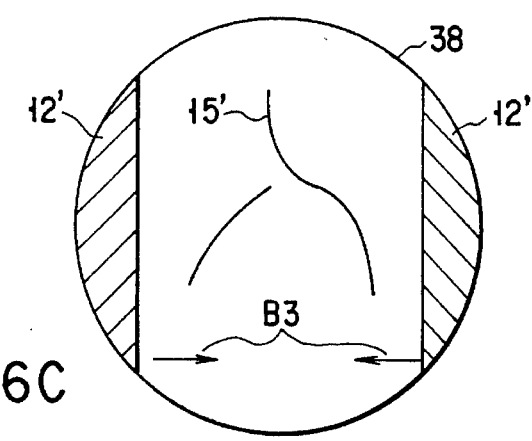

FIG. 6A corresponds to FIG. 2A, showing an image prior to rotation of the support unit 40. FIG. 6B shows an image after rotation correction by the TV camera 30 when the support unit 40 is rotated through 90° on the third axis and corresponds to FIG. 2C. FIG. 6C shows an image when the X-ray beam limiting device 12 is also rotated in conjunction with the TV camera 30 in accordance with the present invention. Arrows B1, B2 and B3 indicate the direction in which the image 12' of the X-ray beam limiting device 12 displayed on the display device 38 closes when the X-ray beam limiting device is instructed to close in the left/right direction by the X-ray beam limiting device movement operation switch 52 on the operating console 50. FIG. 6B shows the conventional image rotation correction based only on the TV camera 30. In this case, even if the X-ray beam limiting device is instructed by the operation switch 52 to open in the left/right direction, the X-ray beam limiting device image 12' will move to close in the up/down direction as indicated by arrows B2. In the present invention, however, the X-ray beam limiting device 12 is controlled to rotate through the same angle as the angle of rotation of the TV camera 30 for image rotation correction.

That is, according to the second embodiment of the present invention, since the X-ray beam limiting device 12 is controlled in conjunction with the rotation of the TV camera 30 so that their relative relationship remains unchanged from the initial state (γ=0°), the image 12' of the X-ray beam limiting device displayed on the display device 38 makes no rotation as shown in FIG. 6C and opens or closes in the same direction as instructed by the movement operation switch 52.

As described above, in the present invention, since the X-ray beam limiting device is always controlled to operate as instructed by the movement operation switch 52, the X-ray beam limiting device image 12' even after the rotation correction moves to close in the left/right direction when the movement to close in the left/right direction is specified by the movement operation switch without moving to close in the up/down direction as in the prior art.

Figure 7:
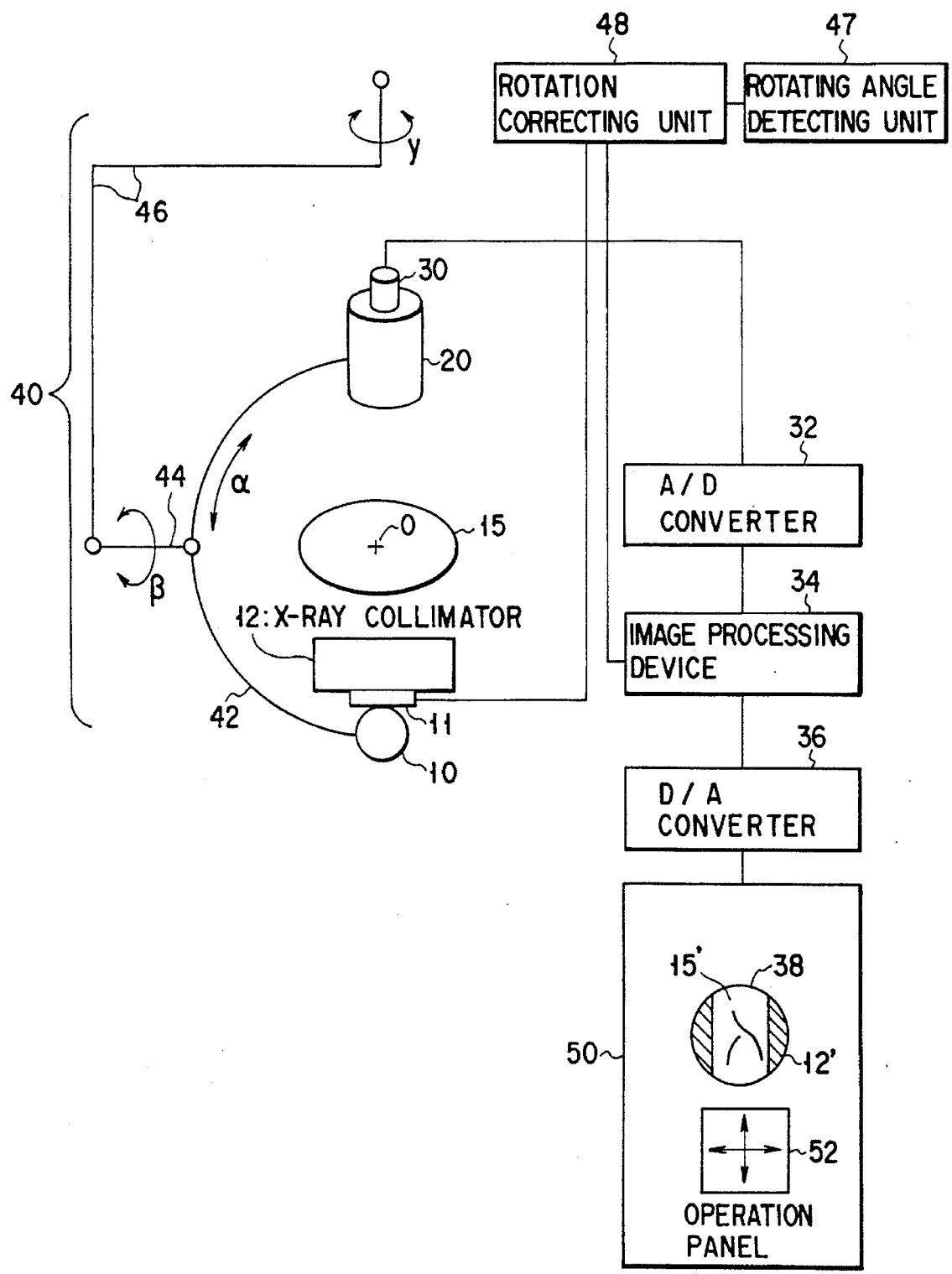
FIG. 7 is a simplified diagram of an X-ray diagnostic apparatus according to a third embodiment of the present invention.

FIG. 7 shows an X-ray diagnostic apparatus according to a third embodiment of the present invention. In FIG. 7, as reference numerals are used to denote corresponding parts to those in FIG. 5A and their description is omitted.

The third embodiment is distinct from the second embodiment in that the image rotation correction is made not by the TV camera but by the image processing circuitry.

Thus, the correction signals from the rotation correction unit 48 are applied to the X-ray beam limiting device rotating device 11 and the image processing unit 34. The image processing unit 34 makes rotation correction on an image to provide such image as shown in FIG. 6B as described in connection with the second embodiment and, at the same time, the X-ray beam limiting device rotating device 11 responds to the signal from the rotation correction unit 48 to rotate the X-ray beam limiting device 12 so that such an image as shown in FIG. 6C can be obtained.

According to the present invention, therefore, since the direction in which the X-ray beam limiting device moves to open or close always coincides with the direction of movement of the X-ray beam limiting device specified by the movement operation switch, maloperations can be avoided. Thus, fast diagnosis is permitted. In addition, the burden on an operator can be lightened.

Although the first, second and third embodiments of the present invention have been described separately, the first embodiment might be combined with the second or third embodiment. In this case, an X-ray diagnostic apparatus of higher operability and reliability could be obtained. The rotation correction unit 48 may be a manual input type.

Although the preferred embodiments of the present invention have been disclosed and described, it is apparent that the present invention may be practiced or embodied in still other ways without departing the scope and spirit thereof.

Additional advantages and modifications will readily occur to those skilled in the art. Therefore, the present invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. An X-ray diagnostic apparatus comprising:

support means having a first arm capable of rotation on a first axis, a second arm attached to said first arm so that it can rotate on a second axis, and a third arm attached to said second arm so that it can slide on an arc centered at a third axis, said first, second and third arms having first, second and third reference positions, respectively;

an X-ray generator, which has an X-ray beam limiting device, mounted on an end of said third arm for irradiating an object under examination with X rays;

movement operation means for instructing said X-ray beam limiting device to move to open or close in first and second directions on a plane perpendicular to the direction of emission of X rays from said X-ray generator;

an image intensifier, mounted on the other end of said third arm so that it is opposed to said X-ray generator, for detecting X rays transmitted through said object under examination to provide an optical image;

a TV camera connected to said image intensifier for converting said optical image into a video signal to provide an X-ray image of said object;

display means for displaying said X-ray image; and rotation correction means for, when said support unit rotates, making a rotation correction to an X-ray image displayed on said display means on the basis of a first rotation angle of said first arm from its first reference position, a second rotation angle of said second arm from its second reference position, and a third rotation angle of said third arm from its third reference position, and wherein said rotation correction means includes means for permitting the direction in which said X-ray beam limiting device displayed on said display means opens or closes, to coincide with the direction specified by said movement operation means all the time.

2. An X-ray diagnostic apparatus according to claim 1, wherein said rotation correction means includes means for rotating said X-ray beam limiting device through a given angle in a given direction in conjunction with the rotation of at least one of said TV camera and said image intensifier.

3. An X-ray diagnostic apparatus according to claim 1, wherein said rotation correction means includes at least one of means for rotating said TV camera, means for rotating said image intensifier, and means for making image rotation correction by means of image processing.

4. An X-ray diagnostic apparatus according to claim 1, wherein, assuming said first, second and third rotation angles to be $\alpha$, $\beta$ and $\gamma$, respectively, and taking $$X = \sin\alpha \cdot \cos\gamma - \sin\beta \cdot \cos\alpha \cdot \sin\gamma,$$

said rotation correction means makes rotation correction on said X-ray image by rotating it through an angle $\phi$, which is determined as follows:

(a) when $X=1$, $$\phi = 180 - \beta \quad (\gamma = 0)$$

$$\phi = \beta \quad (\gamma \neq 0)$$

(b) when $X=-1$, $$\phi = 180 - \beta \quad (\gamma \neq \pm 180)$$

$$\phi = \beta \quad (\gamma \neq \pm 180)$$

(c) when $X \neq \pm 1$, $$\phi = \phi_0 \quad \text{when } \gamma \cdot \cos\beta > 0$$

$$\phi = -\phi_0 \quad \text{when } \gamma \cdot \cos\beta < 0$$

where $$\phi_0 = \cos^{-1}\{(\cos\gamma \cdot \cos\alpha + \sin\beta \cdot \sin\alpha \cdot \sin\gamma)/(1-X^2)^{1/2}\}.$$

5. An X-ray diagnostic apparatus according to claim 4, wherein said rotation correction means includes at least one of means for rotating said TV camera, means for rotating said image intensifier, and means for making image rotation correction by means of image processing.

6. An X-ray diagnostic apparatus comprising:

support means carrying an X-ray generator with an X-ray beam limiting device for irradiating an object under examination with X rays through said X-ray beam limiting device, an image intensifier opposed to said X-ray generator for detecting X rays transmitted through said object to provide an optical image, and TV camera for converting said optical image into a video signal to provide an X-ray image of said object, said X-ray generator, said image intensifier and said TV camera rotating about three mutually orthogonal axes while keeping their relative position;

movement operation means for instructing said X-ray beam limiting device in first and second directions on a plane perpendicular to the direction of emission of X rays from said X-ray generator;

display means for displaying an X-ray image of said object output from said TV camera;

rotation correction means for correcting for the tilt of an X-ray image of said object displayed on said display means due to the rotation of said support unit; and correction means for making the direction of opening or closing of said X-ray beam limiting device displayed on said display means coincident with a direction of movement of said X-ray beam limiting device instructed by said movement operation means all the time.

7. An X-ray diagnostic apparatus according to claim 6, wherein said correction means includes means for rotating said X-ray beam limiting device through a given angle in a given direction in conjunction with the rotation of at least one of said TV camera and said image intensifier.

8. An X-ray diagnostic apparatus according to claim 6, wherein:

said support means has a first arm capable of rotation on a first axis, a second arm attached to said first arm so that it can rotate on a second axis, and a third arm attached to said second arm so that it can slide on an arc centered at a third axis, said first, second and third arms having first, second and third reference positions, respectively, said X-ray generator is mounted on an end of said third arm for irradiating an object under examination with X-rays, and said image intensifier is mounted on the other end of said third arm.

9. An X-ray diagnostic apparatus according to claim 8, wherein, assuming first, second and third rotation angles of said first, second and third rotation directions to be $\alpha$, $\beta$ and $\gamma$, respectively and taking $$X = \sin\alpha \cdot \cos\gamma - \sin\beta \cdot \cos\alpha \cdot \sin\gamma,$$

said rotation correction means makes a rotation correction of said X-ray image by rotating it through an angle $\phi$, which is determined as follows:

(a) when $X=1$.

$$\phi = 180 - \beta (\gamma = 0)$$

$$\phi = \beta (\gamma \neq 0)$$

(b) when $X = -1$, $$\phi = 180 - \beta (\gamma = \pm 180)$$

$$\phi = \beta (\gamma \neq \pm 180)$$

(c) when $X \neq \pm 1$, $$\phi = \phi_0 \text{ when } \gamma \cdot \cos\beta > 0$$

$$\phi = -\phi_0 \text{ when } \gamma \cos\beta < 0$$

where, $$\phi_0 = \cos^{-1}\{(\cos\gamma \cdot \cos\alpha + \sin\beta \cdot \sin\alpha \cdot \sin\gamma)/(1-X^2)^{1/2}\}.$$

10. An X-ray diagnostic method for use with an X-ray diagnostic apparatus comprising: support means carrying an X-ray generator with an X-ray beam limiting device for irradiating an object under examination with X rays through said X-ray beam limiting device, an image intensifier opposed to said X-ray generator for detecting X rays transmitted through said object to provide an optical image, and TV camera for converting said optical image into a video signal to provide an X-ray image of said object, said X-ray generator, said image intensifier and said TV camera rotating about three mutually orthogonal axes while keeping their relative position; movement operation means for instructing said X-ray beam limiting device in first and second directions on a plane perpendicular to the direction of emission of X rays from said X-ray generator; display means for displaying an X-ray image of said object output from said TV camera; and rotation correction means for correcting for the tilt of an X-ray image of said object displayed on said display means due to the rotation of said support unit, said method comprising the step of making the direction of opening or closing of said X-ray beam limiting device displayed on said display means coincident with a direction of movement of said X-ray beam limiting device instructed by said movement operation means all the time.

11. An X-ray diagnostic method according to claim 10, wherein said X-ray beam limiting device is rotated through a given angle in a given direction in conjunction with the rotation of at least one of said TV camera and said image intensifier.

* * * * *